United States Patent [19]

Messner et al.

[11] 4,153,512

[45] May 8, 1979

[54] STORAGE STABLE ANTIBIOTIC SUSCEPTIBILITY TEST KIT AND METHOD OF TESTING

[75] Inventors: Eric J. Messner; Albert C. Dornbush, both of Pearl River, N.Y.

[73] Assignee: Fisher Scientific Company, Pittsburgh, Pa.

[21] Appl. No.: 674,473

[22] Filed: Apr. 7, 1976

[51] Int. Cl.$^2$ .................. C12K 1/04; C12K 1/06; C12K 1/10
[52] U.S. Cl. ................. 195/103.5 K; 195/103.5 M; 195/100; 195/102; 195/127; 195/140
[58] Field of Search ............ 195/103.5 R, 127, 139, 195/103.5 M, 103.5 K, 140

[56] References Cited

U.S. PATENT DOCUMENTS

| | | | |
|---|---|---|---|
| 3,107,204 | 10/1963 | Broun et al. | 195/139 |
| 3,539,450 | 11/1970 | Deutsch | 195/68 |
| 3,713,985 | 1/1973 | Astle | 195/103.5 R |
| 3,936,355 | 2/1976 | Lawson | 195/100 |
| 3,937,655 | 2/1976 | Pfeiffer et al. | 195/103.5 K |
| 3,992,265 | 11/1976 | Hansen | 195/103.5 R |

*Primary Examiner*—Raymond N. Jones
*Assistant Examiner*—Robert J. Warden
*Attorney, Agent, or Firm*—Webb, Burden, Robinson & Webb

[57] ABSTRACT

The susceptibility of microorganisms to various antibiotics is determined by propagating microorganisms in the presence of different concentrations of various antibiotics in a plurality of test chambers, using a serial dilution technique. Microgram quantities of each antibiotic are retained in a graduated series of concentrations in each of a series of test chambers by poly(vinyl pyrrolidone) as a water-soluble bulking agent and carrier, in frozen-dried form.

7 Claims, 13 Drawing Figures

ANTIBIOTIC IN FREEZE-DRIED POLY (VINYL PYRROLIDONE) FOAM

STORAGE STABLE ANTIBIOTIC SUSCEPTIBILITY TEST KIT AND METHOD OF TESTING

RELATED APPLICATIONS

Related applications of other inventors, but common assignment, including Ser. No. 645,581—ANTIBIOTIC SUSCEPTIBILITY TEST, Lloyd Frank Hansen, Dec. 31, 1975 now U.S. Pat. No. 3,992,265 Nov. 16, 1976; and Ser. No. 659,452—DISPOSABLE ANTIBIOTIC SUSCEPTIBILITY TEST PACKAGE, John Eugene Studer, Jr., Feb. 19, 1976, show test wells or chambers for holding antibiotics for use with serial dilution techniques, and have claims to specific test cell devices.

BACKGROUND OF THE INVENTION

This invention relates to antibiotic susceptibility testing and more particularly test kits having a series of various concentrations of various antibiotics or therapeutic control agents which are used to ascertain the interaction between such control agents and various microorganisms, usually pathogenic.

With the proliferation of antibiotics and other drugs both in the hospital and in the laboratory as well as educational institutions there is an increasing demand for information concerning the susceptibility or sensitivity of a particular microorganism to various antibiotics or drugs, as well as information on the assay of particular constituents in blood, or other biological liquids.

PRIOR ART

The use of antomated analytical procedures has become of increasing importance. For both chemical and biological procedures the number of samples to be run has been increasing exponentially as new procedures are developed, and existing procedures are adapted to large quantity requirements.

U.S. Pat. No. 3,272,719—METHOD AND APPARATUS FOR DETERMINING THE SENSITIVITY OF BODY FLUID INFECTANTS TO DRUGS, Avakian, Sept. 18, 1966 shows rectangular or square compartments, with a common wall between adjacent rows and files. A notch is provided for a string saturated with infected fluid to sag into compartments containing a sterile nutrient and known concentrations of drugs under test.

U.S. Pat. No. 3,301,065—LIQUID SAMPLE SUPPLY APPARATUS, Fahrenbach, Bell and Sandage, Jan. 31, 1967, shows an automatic sampling system in which a series of cups containing samples are fed serially into an analytical system. The samples may be in cups or a spiral in a plate, or may be fed as a series of individual pallets locked together and fed along a belt. Locking the pallets together insures coordination in feeding separate pallets.

Belgium Pat. No. 691,532, Feb. 28, 1967, shows lyophilized (freeze-dried) antibiotics or chemotherapeutic agents in various concentrations, including a blank, in separate cells arranged in columns and rows in a tray, for testing the resistance of microorganisms to antibiotics or agents. Retaining appendices project from the base of the culture cells to retain the lyophilized material in the individual cells. Identifying covers cooperate with each cell to close, and identify the contents of, each cell. A culture medium and/or indicator may be present in the lyophilized state in the test cells. The cells and the covers are essentially transparent to permit observation of the cultures.

U.S. Pat. No. 3,453,180—TEST ARTICLE, Fraser and Atkinson, July 1, 1969 shows a bibulous test strip for determining glucose levels in urine having as an impregnant the dried residue of a liquid mixture which comprises liquid glucose oxidase, peroxidase, citric acid-sodium citrate buffer system, o-tolidine hydrochloride, poly(vinyl pyrrolidone), an acid and/or partial ester derivative of an interpolymer of methyl vinyl ether and maleic anhydride, sodium lauroyl sarcosinate, and a long-chain polymer of 3,6-anhydro-D-galactose and sulfated D-galactose residues.

U.S. Pat. No. 3,533,744—METHOD AND APPARATUS FOR PERFORMING ANALYTICAL OPERATIONS, Unger, Oct. 13, 1970, in FIG. 2 shows a sample carrier for automatically analyzing blood, which carrier is in the form of an integral rectangular slide, having thirty elongated juxtaposed shallow receptacles for receiving fractions of one single sample. The plastic sample carriers are disposable and of transparent plastic material.

U.S. Pat. No. 3,546,131—STABILIZED CYANMETHEMOGLOBIN REAGENT CONTAINING FERRICYANIDE, CYANIDE AND POLYVINYLPYRROLIDONE, Stern and Reardon, Dec. 8, 1970, shows a dry formulated reagent containing ferricyanide and cyanide for use in the photometric determination of hemoglobin in blood, comprising a water soluble macromolecular desiccant such as polyvinylpyrrolidone, the polyacrylamides, gelatin, dextrin, the alkali metal salts of cellulose, and hydrolyzed polyvinyl alcohol derivatives, to enhance resistance to light, heat and cold, and aging.

U.S. Pat. No. 3,578,412—AUTOMATED TRANSPORT SYSTEM, Martin, May 11, 1971, shows an automated chemical analyzer having individual sample capsules, with several chambers in each sample capsule.

U.S. Pat. No. 3,649,464—ASSAY AND CULTURE TRAY, Freeman, Mar. 14, 1972, shows a transparent tray having rows and columns of upstanding cups or wells, which are spaced apart to avoid cross-contamination. A peripheral wall around the tray permits stacking of a set of trays. A strip having a series of well seals is shown to seal off an individual row of wells.

U.S. Pat. No. 3,713,985—DEVICE AND METHOD FOR TESTING POTENCY OF BIOLOGICAL CONTROL REAGENTS, Astle, Jan. 30, 1973, shows a series of biological reagents in a series of cups, in a strip, or pallet, with the strip having dovetails to longitudinally lock a group of the strips together to form a tray. A foil cover to protect lyophilized contents during storage is disclosed, with reconstitution of the contents at time of use. The culture medium and the test organism are added sequentially and separately at time of use, so that the control reagent is first redispersed. It is then inoculated, and incubated.

U.S. Pat. No. 3,890,201—MULTI-CHAMBER IMPEDANVCE MEASURING MODULE-CAP COMBINATION, Cady, June 17, 1975, shows rows and columns of upstanding cylinders on a flat base, forming cells, with electrically conductive strips in each cell to permit impedance measurement of the cell contents. The impedance in the cell is a function of microoganism growth. Separate caps are provided for each cell to permit gas flow into the individual cells during incubation.

SUMMARY OF THE INVENTION

It has now been found that the reliability and ease of use of an antibiotic susceptibility test kit is markedly improved by using poly(vinyl pyrrolidone) as a water-soluble bulking agent and antibiotic retaining carrier for an antibiotic in test chambers.

The quantity of antibiotic present for inhibition of the growth of pathogenic microorganisms is often in the range of about 0.1 to about 250 micrograms per milliliter. With 0.2 ml of solution being a convenient size test sample, the quantity of antibiotic in a series of chambers is between about 0.02 and 50 micrograms. These quantities are so small that the unaided eye would not be able to confirm their presence in the test chambers.

By using poly(vinyl pyrrolidone) as a water-soluble bulking agent and antibiotic retaining carrier, particularly when the poly(vinyl pyrrolidone) and antibiotic are loaded into test chambers in aqueous solution, and then frozen and dried; the antibiotic is bulked into the poly(vinyl pyrrolidone) foam, and both adhesively held in the test chamber, and conclusively shown to be present in the test chamber by visual observation at time of use. The visibility of the foam gives physical confirmation of the presence of the antibiotic, and a psychological enhancement to the user.

The dried poly(vinyl pyrrolidone) aids in solution of the antibiotic, as it keeps the antibiotic finely subdivided and is soluble itself. Poly(vinyl pyrrolidone) is biologically inert. It has been used as a blood extender, and in many biological environments. It is listed in the U.S. Pharmacopoeia as "Povidone", and biological uses are well known. It is so inert that a quantity from less than 250 to at least 10,000 micrograms per milliliter is satisfactory for forming a sponge to hold the antibiotic. A preferred concentration of 2,000 micrograms per milliliter is convenient. A typical test chamber holds about 0.2 milliliter of solution. This gives 400 micrograms per 0.2 milliliter test-container—which is convenient both from the point of constitution and reconstitution, and also is ready visible as a foam to confirm the presence of both the poly(vinyl pyrrolidone) and the antibiotic.

Preferably the same concentration of poly(vinyl pyrrolidone) is used in each test chamber to reduce the number of variables, and permit visual observation to confirm that each well is uniformly filled.

Often a well is used which has no antibiotic to confirm growth characteristics in the absence of any inhibition, or to confirm sterility of the test kit. This test chamber may optionally contain poly(vinyl pyrrolidone) as a blank.

Obviously the test kit should be sterile so that only the test organism is cultured. Sterile techniques are used in filling and drying. Some antibiotic or growth controlling substances in the nature of, and acting as a microorganism inhibiting agent may be sterilized in situ by ethylene oxide, radiation, heat or other agent compatible with the growth controlling substance. Certain of the sulfa drugs are very stable under sterilizing processes.

While not limited thereto, one test plate useful with the present invention is a molded transparent plate of a biologically inert plastic such as a polymer of methyl methacrylate, or a vinyl resin, but which may be of any biologically inert transparent or nearly transparent plastic, which plate has a row of approximately rectangular wells. The wells preferably have a slight taper, which permits molding in simplified molds. By having about $\frac{1}{2}°$ to 4° draft or molding taper on all vertical surfaces, a two piece mold can be used to economically produce the test plates. A slight taper permits the use of a mechanical light source, and optical reader or scanner, with negligible inaccuracies from the taper. Parallel sides which are more optically true can be used, and while optically more desirable, increase the cost of production of the test plates. Visual inspection or "eyeball" reading is often used to detect inhibition of growth in the several wells.

For incubation a well cover protects from chance contamination. A flexible plastic such as polyethylene is low in cost, and readily molded. The well cover is shaped to fit an entire plate row of wells, often 8 or 10, and has a rim to fit into each well, thus closing the well and positioning the well cover. A lifting flap on the well cover permits the well cover to be readily lifted from the test plate. The well cover is reversible, so that in one position the lifting flap is flat against the test plate, and when rotated 180°, extends outwardly as an indexing flap. The flap may be treated to improve the adhesion of an ink or label.

By having a number of test plates with wells in each, a separate antibiotic can be used in each test plate. Different patients in a hospital may have different spectra of antibiotics to be tested.

By being stackable, a stack of 5 or 10 can be handled as a unit in incubation and storage. A plurality of test plates, 5 or 10, are conveniently stacked with a dehydrating agent in a bag until time of use. A foil bag may be used to give maximum protection from moisture.

DRAWINGS

Figure 1:
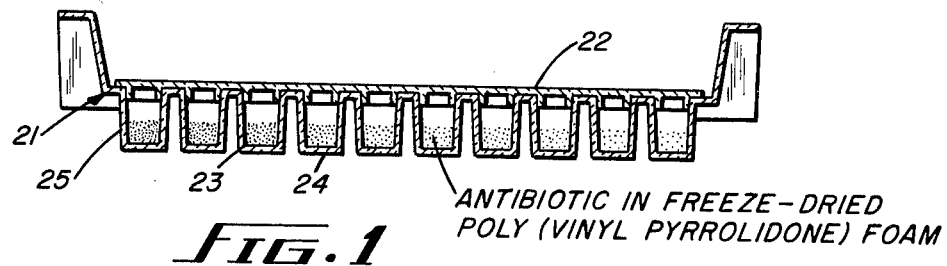
FIG. 1 is a sectional view of a culture test plate with a plastic snap cover closing the individual wells, showing the antibiotic in a poly(vinyl pyrrolidone) foam.
Figure 10:
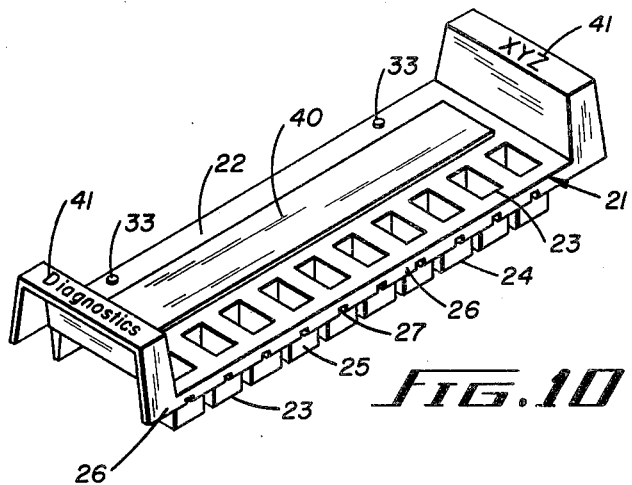
FIG. 10 is a pictorial view of a single culture test plate.

As shown in FIGS. 1 and 10 the biological culture test plate 21 consists of a flat platform 22 having therein a series of rectangular wells 23. Each rectangular well has a flat bottom 24 and approximately rectangular walls 25. By using approximately parallel walls, light can be passed through two approximately parallel walls with a minimum distortion or bending; which permits either inspection by eye or a mechanical optical device to measure the turbidity of materials within the well. It is desirable that the well have a slight taper within the range of about ½° to 4° such as taper permits the molding of wells, and the withdrawal of the molding mandrel. If there is no taper, it is more difficult to withdraw the mandrel; and if the taper is more than about 4° the well starts to become somewhat prismatic in its action on light.

As shown in FIG. 1 for the specific embodiment shown, there is a series of 10 wells. Obviously, the number of wells may vary but 10 is a convenient number for most test purposes.

At the front of the flat platform 22 is a dependent or downwardly extending front skirt 26. The front skirt gives additional rigidity, and also has therein a group of indexing notches 27. Each indexing notch is in a coordinated spacial relationship with a well. Conveniently the notches are centered with respect to each well and serve the purpose of indexing the test plate with respect to a reading device when a mechanical feed system is used in connection with an electrooptical density reading system.

Conveniently, but not necessarily, at the back of the flat platform is a rear skirt 28. Also adjacent the rear of the platform is a stiffening rib 29. This rib is slightly tapered for convenience in molding and extends downwardly from the flat platform a sufficient distance that the test plate rests horizontally on a horizontal flat surface. Preferably, the stiffening rib and the wells have a common bottom plane. This provides for the culture test plates to rest flat on a work surface during filling and culturing, and also that permits the test plates to be stacked without tipping.

In the ends of the test plate are stacking handles 30. These handles are interiorly hollow and tapered whereby the handles nest when test plates are stacked. The front and rear of the handles conveniently are extensions of the front skirt and rear skirt 26 and 28 and have a rise member 31 and a flat top 32 on each end. The skirt extensions are at such an angle that when stacked, the assembly nests without binding but without undue free motion.

The top of the flat platform above the stiffening rib may have spacing buttons 33. These spacing buttons 33 are such size that when the well snap covers 34, referred to below, are placed in the wells the stiffening rib contacts the spacing buttons and gives uniform vertical stacking.

For shipment, incubation, and storage, the wells are closed and the contents protected by a well snap cover 34. The well snap cover is of a thin sheet 35 of flexible plastic. It is slightly larger than the wells to be covered and has depending therefrom a series of rectangular well seals 36.

Figure 2:
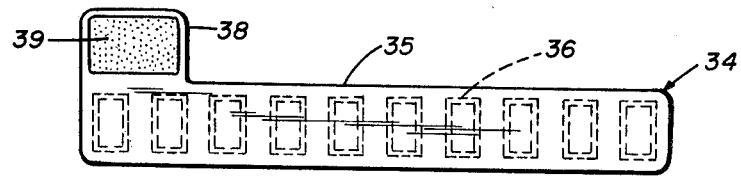
FIG. 2 is a view of a plastic snap cover.
Figure 5:
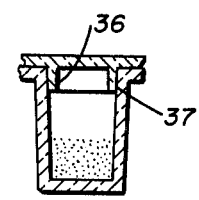
FIG. 5 shows a sectional view of the well with the snap cover in place.

As shown in FIGS. 2 and 5 each well seal has a rectangular configuration and such size as to fit into a rectangular well 23. The spacing between them corresponds to the spacing in the series of rectangular wells 23. The well seals are conveniently hollow and extend part way into the well in assembled position. The rims 37 conveniently are an easy press fit into the rectangular well 13 so that the snap cover 34 may be easily removed and replaced, and when placed in position will not fall out under shipping and handling stresses. Also on the snap cover is a lifting flap 38. The lifting flap has in part a textured area 39. The textured area is formed in molding by texturizing the mold so that the texturized area is roughened and accepts ink or a label more readily than the smooth surface of the snap cover. The lifting flap conveniently extends from the snap cover about the width of the snap cover and when placed inwardly fits against the cultured test plate so that the lifting flap 38 can be picked up with a fingernail; but can be rotated 180° upon a vertical axis so that the lifting flap extends outwardly as an identification tab.

The textured area on the lifting flap of the snap cover permits the identification of a particular culture test plate in a stack. Conveniently but not necessarily, on the face of the culture test plate 21 is a label 40. Conveniently the label includes the name of the antibiotic or active agent, identification as to batch number, dates and origin and has a room for the name of the patient, the date of the test and other information at the time of use.

The ends of the handles 30 may have a molded legend 41 therein. It is convenient for a trademark or name of the manufacturer to be molded into the surface of the handle for identification.

Figure 3:
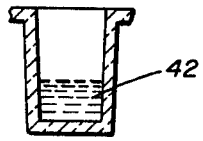
FIG. 3 is a sectional view of a well filled with a liquid solution of antibiotic and poly(vinyl pyrrolidone).

The use of the culture test plate is shown in FIGS. 3 through 8. The culture test plate is molded with 10 rectangular wells. As shown in FIG. 3 the well is filled with a liquid antibiotic solution 42 containing poly(vinyl pyrrolidone) as a water soluble bulking agent and antibiotic retaining carrier. Poly(vinyl pyrrolidone) is biologically inert and has no effect on the antibiotic, the culture medium or the microorganisms; and yet when frozen and dried, fills the well with a sponge which resembles cotton candy in texture which holds the antibiotic in place and prevents migration of the antibiotic.

Figure 4:
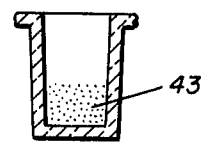
FIG. 4 is a sectional view of the well after the liquid has been frozen and dried to form a foam.
Figure 13:
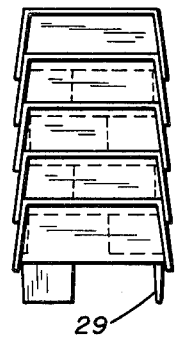
FIG. 13 is an end view of a stack of 5 culture test plates stacked for shipment or handling.
Figure 11:
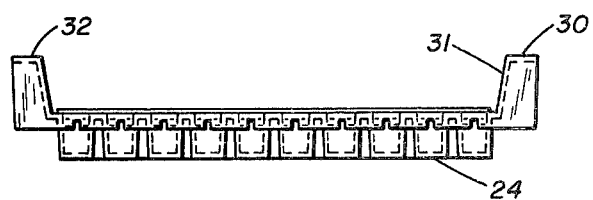
FIG. 11 is a slide elevation of a single culture test plate.
Figure 12:
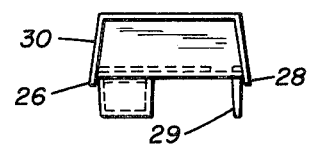
FIG. 12 is an end view of a culture test plate.

As shown in FIG. 4 the liquid filled into the wells is frozen and dried to form a dried antibiotic in the poly(vinyl pyrrolidone) 43. Conveniently, a group of the culture test plates are stacked with the well snap covers removed, as for example as shown in FIG. 13, and a group of such stacks are placed on the shelves of a freezing chamber, the contents frozen, the chamber evacuated and using conventional lyophilizing techniques dried to a sponge. The dryness of the sponge is protected by replacing the well snap covers and storing in a dry environment until time for use.

FIG. 5 shows the dried sponge with the well snap cover in position.

Figure 6:
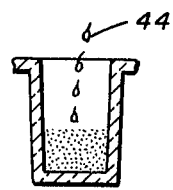
FIG. 6 shows the contents of a well being reconstituted by the addition of a liquid.

At the time of use, as shown in FIG. 6, a liquid diluent is added to the dry sponge.

Usually, using tube dilution practice, the liquid diluent is an appropriate culture medium 44 which has been inoculated with a test organism. Preferably the test organism is at a standard concentration so that the test plate results are quantitative as well as qualitative.

Theoretically, the culture medium itself may be mixed with the antibiotic and dried down and retained in storage so that only the test organism and in an inert diluent, namely water, need be added at the time of use. It is preferred that the culture medium be added with the test organism (1) because the test organism can be added to the culture medium before it is added, to avoid a double addition, (2) a culture medium can be chosen which is particularly appropriate for a specific test organism, and (3) the test organism concentration is uniform for all tests. Many dehydrated culture media are hygroscopic, and by their attraction of moisture could hasten the destruction of some antibiotics. Different laboratories prefer different culture media for different organisms or even the same organism. By adding the organism being tested in the culture medium there is additional flexibility in selecting the culture medium. Also, without the culture medium, there is a minimum risk of having a system present which could support bacterial growth during storage.

Figure 7:
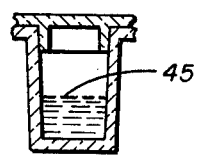
FIG. 7 shows a view in section of a well with the snap cover in place, showing the clear liquid either before the growth of any microorganisms or with the growth having been inhibited.
Figure 8:
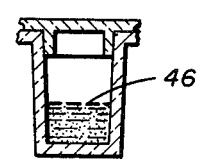
FIG. 8 shows a single well with the snap cover in place with a cloudy or turbid liquid resulting from the propagation of microorganisms therein.

In FIG. 7 is shown a well having a clear solution 45 therein. After the sponge and antibiotic have dissolved in the culture medium, the solution is clear. If there is sufficient antibiotic to inhibit growth of the test organism, the solution remains clear, if not, the microorganism grows and causes the solution to become cloudy 46 as shown in FIG. 8.

A clear solution 45 shows no bacterial growth. The cloudy solution 46 shows bacterial growth.

The reading of the solutions to determine bacterial growth may be either by inspection with the human eye, in effect an "eyeball" reading, or it may be done by electrooptical equipmemt such as a photosensitive reader and a constant intensity light. The light may have a selected wave length or color depending upon the solution. Separate readers may be used for each cell or the same reader may be used for a group of 10 cells in a culture test plate serially.

Figure 9:
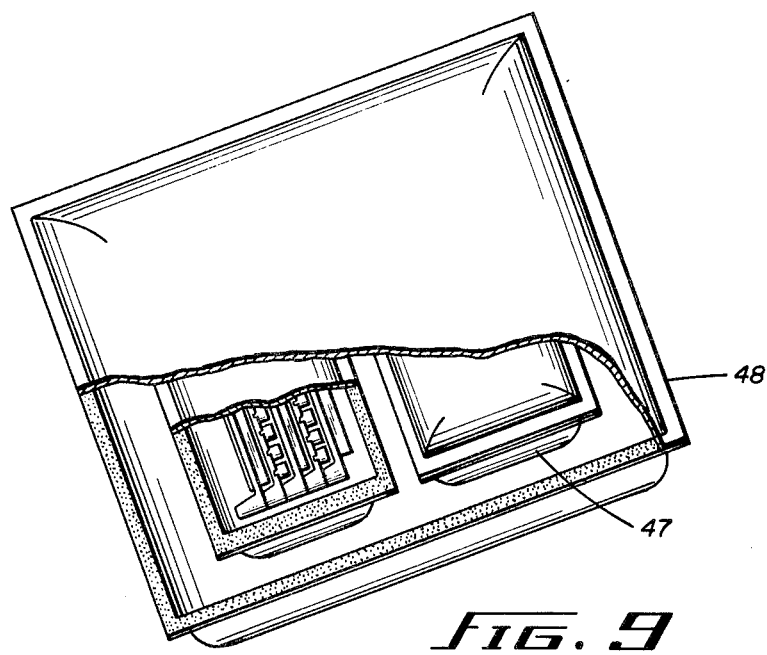
FIG. 9 is a pictorial view showing a group of test plates in each of two plastic bags which are sealed inside of a moisture proof foil envelope.

For shipment and storage a group of 5 test plates in a stack are conveniently enclosed in a plastic envelope 47 as shown in FIG. 9. A dessicant may also be placed in the envelope to insure dryness. Two or more such plastic envelopes may then be placed in a foil outer envelope 48. The foil outer envelope may have additional dessicant envelopes in it and is sealed so as to protect its contents from ambient moisture for an extended length of time.

When so sealed, the present culture test plates maintain essentially their original labeled potency for several months, and it can be expected that the test plates will be satisfactory for at last several years.

The size of the wells is not critical but a well size of 8×10 mm. at the top and 5×8 mm. at the bottom with 9 mm. depth permits working with 0.2 ml. of fluid with the wells about half full, and permits a convenient working size with the consumption of a minimum quantity of reagents and materials. A thickness of the cells themselves, the test plate, and the handles through out, of about 0.8 mm. (1/32 inch) gives good results. Such a thickness is a compromise between having the parts thick enough for strength and thin enough to require a minimum of material. With such a thickness the culture test plates are strong enough to be reused if desired but are sufficiently inexpensive that it is usually cheaper to consider the test plates as disposable.

The basis of the culture test plate method is the broth or tube dilution technique. Details of standardized methods and recommendations for use of this procedure are found in (1) Ericson, H. M. and Sherris, J. C., "Antibiotic Sensitivity Testing, Report of an International Collaborative Study," *Acta Path. Microbiol. Scand. Sect. B, Suppl.* 217 (1971); and (2) Manual of Clinical Microbiology, Second Edition, Lennette, E. H., Spaulding, E. H., and Truant, J. P., Eds. American Society for Microbiology (1974).

EXAMPLE

The antibiotic to be tested is provided in the two-fold dilution range of interest by starting with 10 four liter flasks into the first of which was added 6 g. of poly(vinyl pyrrolidone) (Povidone USP) and 3 liters of triple distilled water. In each of the other nine flasks was added 3 g. of poly(vinyl pyrrolidone) and 1,500 ml. of triple distilled water.

To the first flask was added 206.25 mg. of tetracycline hydrochloride, after which the flask was shaken until the contents were dissolved and uniformly distributed. One half of the contents of the first flask was then added to the second flask and the contents of the second flask shaken until uniform. One half of the contents of the second flask was then added to the third flask, etc., and the series continued until the serial two-fold dilution was obtained in the ninth flask. The excess diluted solution in the ninth flask was discarded. The tenth flask had only poly(vinyl pyrrolidone) and triple distilled water. It may be left empty.

The contents of each flask was sterile filtered into two liter reagent bottles which were capped and kept in an ice-water bath for filling by sterile techniques. Filling should not be unduly delayed. The solutions normally remain stable and without change for at least 24 hours if kept cold, but it is preferable that they be filled immediately to guarantee against loss of potency.

2/10 ml. of the contents of each of the flasks were filled into the respective wells of a single test plate.

The wells in a total of five thousand test plates were filled, the test plates stacked and placed in racks in a cold chamber. The cold chamber was pre-chilled with the cold chamber being maintained at colder than −40° C. with shelf cooling being maintained until the contents of all of the wells in all of the test plates were frozen solid. This should occur in less than 12 hours. After freezing, the cold chamber was evacuated to less than 100 microns total pressure, after which the shelf temperatures was raised to about 10° C. and maintained at this temperature until temperature probes in the assembly indicate that the temperature within the wells was within about 5°-10° C. of the temperature of the shelves themselves. The shelves were then warmed up to about 30° C., and after the test plates had warmed up appropriately, the temperature was increased to 40° C. and the chamber held for 4 hours. At this point the contents of each well were thoroughly dry.

While continuing the use of sterile techniques, well snap covers were placed over the dried test plate wells and a set of 5 test plates were stacked for convenience and placed in a polyethylene plastic envelope. A 5 g. silica gel packet was placed in each of the plastic envelopes to aid in maintaining dryness. Two such envelopes containing 5 test plates each were then placed in an outer foil pouch which foil outer envelope is essentially impermeable to moisture and maintains dryness of the test plates for an extended period of at least months and predictably for at least several years, if not indefinitely.

The culture test plates have a label on each which indicates the particular antibiotic and its concentration in each of the wells, with space for identification data as to date, the patient and test conditions under which the culture test plate is used. A number of foil envelopes are packaged in a shipping container, the number being based on the usage of customers.

When filled in this fashion, the wells contain:

TABLE I

| Well No. | Tetracycline hydrochloride | |
|---|---|---|
| 1 | 12.5 mcg. | + 10% excess plus 400 mcg. providone |
| 2 | 6.25 mcg. | " |
| 3 | 3.125 mcg. | " |
| 4 | 1.56 mcg. | " |
| 5 | 0.78 mcg. | " |
| 6 | 0.39 mcg. | " |
| 7 | 0.195 mcg. | " |
| 8 | 0.098 mcg. | " |

TABLE I-continued

| Well No. | Tetracycline hydrochloride | |
|---|---|---|
| 9 | 0.049 mcg. | " |
| 10 | 0.00 mcg. | " |

Culture test plates conveniently are used for any antibiotic or therapeutic control agent such as penicillin, ampicillin, clindamycin, erythromycin, methicillin, tetracycline, demethylchlortetracycline, 7-dimethylamino-6-demethyl-6-deoxytetracycline, minocycline, cephalothin, gentamycin, colistin, carbenicillin, chloramphenicol, kanamycin and any of the sulfonamides.

Other antibiotics, either those known or those yet to be discovered may be used—any if the the antibiotics require a range other than that listed, the concentration may be modified—but with the wide range covered by the nine dilutions in the cavities, the proper dosage of most antibiotics will be obtained.

The tenth cup has no antibiotic and hence if inoculated with the test microorganism, shows the growth of the microorganism under uninhibited conditions; or if not inoculated is used to show that no contaminants are present.

The number of culture test plates and choice of culture test plates, each with a difference antibiotic, depends upon the preferences of the medical staff of the using facility.

At the time of use, aliquots of broth inoculated with the bacterial culture to be tested are pipetted into each plate well following which the plates are incubated for a specific time at an indicated temperature. The test is read by visual inspection for growth as indicated by turbidity or no growth as shown by a non-turbid suspension. The endpoint is defined as the well containing the lowest concentration of antibiotic with no detectable microbial growth. The control well on each plate, having no antimicrobial agent present, serves as a measure of the uninhibited growth of the bacterial culture.

PROCEDURE

Specimens obtained in the laboratory from clinical sources are cultured on primary agar plates. Isolated colonies of the organism suspected of being implicated in an infectious process should be selected.

Ideally, identification procedures should be performed concurrently with susceptibility testing.

Mixtures of different types of organisms (mixed cultures) should not be used for susceptibility testing unless there is a clinical emergency. In these instances, or in circumstances where testing is done directly from clinical specimens susceptibility tests should be repeated using a pure culture.

Aerobic, facultatively aerobic and clinically significant obligative anaerobic bacteria may be used for susceptibility testing. Anaerobic bacteria should be suspended in freshly boiled medium, dispensed into plate wells and incubated under anaerobic conditions within 15 minutes.

Three to five colonies of the organism to be tested are suspended in 4 to 5 ml. of sterile trypticase soy broth. The tube containing this inoculum is covered and placed in a water bath for incubation at 34°-46° C. for two or three hours or until a turbid suspension is produced.

The bacterial density of the inoculum is preferably standardized at $1 \times 10^5$ Colony Forming Units (CFU) per milliliter prior to use.

The required $1 \times 10^5$ CFU/ml. suspension of bacteria can be standardized by preferably adjusting to $10^5$ CFU/ml. with the use of a standardized nephelometer.

Alternatively a $BaSO_4$ standard as used for the Kirby-Bauer disc diffusion test can be employed.

0.5 ml. of 0.084 M $BaCl_2$ or 1.17% (w/v) $BaCl_2.2H_2O$ is added to 99.5 ml. of 0.36% (1% v/v) $H_2SO_4$. This suspension is equivalent to approximately $10^8$ Enterobacteriaceae per ml.

The $BaSO_4$ turbidity standard should be dispensed into tubes of the same size used to grow the broth inoculum and stored in the dark for no longer than six months at 20°-25° C. These turbidity standards must be vigorously mixed prior to use.

The inoculum, when standardized by visual comparison against the $BaSO_4$ turbidity standard ($10^8$ CFU/ml.), should be then diluted 1:1000 by mixing 0.1 ml. of the bacterial suspension with 99.9 ml. of fresh sterile broth. The diluted suspension now contains $10^5$ CFU/ml.

Broth media used for dilution of the initial bacterial suspension is Mueller-Hinton broth, except when testing with organisms such as streptococci, neisseria, hemophiline rods, and certain other fastidious organisms. Trypticase soy broth may be used for streptococcal cultures. Supplementation of media for growth of fastidious species should be done according to recommendations of the International Collaborative Study, supra.

The plastic snap covers are removed from each culture test plate and are placed on a clean surface, preferably in an inverted position.

Each well of the plate is then filled with 0.2 ml. (200 µl) of broth standardized to contain $10^5$ CFU/ml. of the microorganism under test.

A repetitive pipetting device may be used to introduce the inoculated broth into the plate wells providing the delivery at the indicated volume is within ±5% and the device can be sterilized prior to use without affecting the delivery, or a manual pipette may be used.

The plastic covers are then snapped back into place using the same covers originally removed from the plate and the plates put in an incubator at 35°-36° C.

Grossly discernible growth is observed in most instances in four to six hours with rapidly growing bacteria. A Minimum Inhibitory Concentration (MIC) endpoint taken at this time has been shown to be equivalent to endpoints taken after 18 hours of incubation in tests done with microorganisms whose growth is rapid. In addition, tests with bacteria exhibiting a slower rate of growth indicate that preliminary MIC's can be found after four to six hours of incubation although plates should be incubated for the full 18 hours to obtain the final result.

The endpoint is defined as the well containing that concentration of antimicrobial agent where there is no detectable microbial growth estimated visually as confluent turbidity or reasonable amounts of flocculation or clusters of bacteria.

A slight haze or a small number of particles seen at the bottom of a well does not constitute growth.

The MIC in mcg. or units per ml. is obtained by multiplying the corresponding content figure imprinted next to the well showing no growth by 5.

In addition to determination of MIC, a Minimum Bactericidal Concentration (MBC) can be determined by removal of a loopful of organisms from two or more wells on either side of the MIC breakpoint, plating them out on a solid medium and observing for viable organisms after an incubation period.

In use is a laboratory or hospital it is customary to have a plurality of test plates such as above described and in which have been placed a group of differnt antibiotics or chemotherapeutic agents and the various test plates containing antibiotics to be tested are cultured together and read either by visual inspection, a so called "eyeball" test, or by using a radiation source such as an electric light and a suitable radiation detector with the test well placed between the radiation source and the detector. For small operations it is convenient to use a single electrooptical reader. For larger installations a group of 10 so that all ten of the wells in a test plate may be read simultaneously is convenient.

The report of the minimum inhibitory concentration of each antibiotic or chemotherapeutic agent is reported so the attending physician can select an antibiotic which is most effective for a particular patient.

The use of the poly(vinyl pyrrolidone) of this invention overcomes two major problems found in the preparation and use of prior art test kits.

First, since the amount of antibiotic in the wells is in minute (microgram) quantities and is serially diluted and frozen-dried in the succession of chambers, it is difficult to visually determine from a quality control standpoint, whether a given chamber contains any antibiotic. The addition of poly(vinyl pyrrolidone) as a bulking agent makes visual detection easier.

Secondly, the use of poly(vinyl pyrrolidone) in conjunction with an antibiotic produces a freeze-dried foam plug of a consistency not unlike cotton candy, which fits snugly into and adheres to the bottom and sides of the chamber. This combination is much less likely to be dislodged from the well during the sealing and unsealing of the plates, and shipment and storage.

Poly(vinyl pyrrolidone) is readily put into aqueous solution with the antibiotic and later inoculated with the aqueous nutrient broth. Further, poly(vinyl pyrrolidone) does not react with the antibiotic, nor affect its potency, nor the growth characteristics of pathogenic organisms.

We claim:

1. A test kit for measuring the antibiotic susceptibility of a microorganism comprising a plurality of integral test chambers, with at least some of said chambers having therein a graduated series of concentrations of an antibiotic and a uniform quantity of poly(vinyl pyrrolidone) as a water-soluble bulking agent and antibiotic retaining carrier, with the antibiotic in dispersed and reconstitutable frozen-dried form in the poly(vinyl pyrrolidone).

2. The test kit of claim 1 in which the antibiotic is present in a two-fold series of dilutions including at least part of the range of 1 to 10 micrograms per milliliter.

3. The test kit of claim 2 in which the test chambers hold about 0.2 milliliters of solution and the range of antibiotic is about 0.05 to 12.5 micrograms per chamber and the range of concentration of poly(vinyl pyrrolidone) is from about 50 to about 2,000 micrograms per chamber containing 0.2 milliliter of solution.

4. The test kit of claim 3 packaged in sterile dry conditions in a moistureproof container.

5. A method of testing the antibiotic susceptibility of a microorganism by a serial dilution technique comprising: forming a series of concentrations of solutions in water of an antibiotic in a uniform concentration of poly(vinyl pyrrolidone) as a water-soluble bulking agent and antibiotic retaining carrier, loading uniform quantities of said series of concentrations in a series of integral test chambers, freezing and freeze-drying said series of concentrations, storing until time of use, and reconstituting the antibiotic in the poly(vinyl pyrrolidone) by adding a culture medium inoculated with a test microorganism, incubating, and then reading the test microorganism growth.

6. The method of claim 5 in which the antibiotic is present in a two-fold series of dilutions including at least part of the range of 1 to 10 microorganism per milliliter.

7. The method of claim 6 in which the test chambers hold about 0.2 milliliters of solution and the range of concentrations of antibiotic is about 0.05 to 12.5 micrograms per chamber and the range of concentration of poly(vinyl pyrrolidone) is from about 50 to about 2,000 micrograms per chamber containing 0.2 milliliter of solution.

* * * * *